United States Patent
Suwan et al.

(10) Patent No.: US 12,186,707 B2
(45) Date of Patent: Jan. 7, 2025

(54) OLEFINS-PARAFFINS SEPARATION PROCESS BY MEMBRANE

(71) Applicant: PTT Global Chemical Public Company Limited, Bangkok (TH)

(72) Inventors: Puttipong Suwan, Bangkok (TH); Suepsakun Chindapon, Bangkok (TH); Sitthipol Simakajonkiat, Bangkok (TH); Nattawat Katinhom, Bangkok (TH)

(73) Assignee: PTT Global Chemical Public Company Limited, Bangkok (TH)

( * ) Notice: Subject to any disclaimer, the term of this patent is extended or adjusted under 35 U.S.C. 154(b) by 529 days.

(21) Appl. No.: 17/488,088

(22) Filed: Sep. 28, 2021

(65) Prior Publication Data

US 2022/0016575 A1    Jan. 20, 2022

Related U.S. Application Data

(63) Continuation of application No. PCT/TH2020/000016, filed on Mar. 17, 2020.

(30) Foreign Application Priority Data

Mar. 29, 2019 (TH) .............................. 1901001970

(51) Int. Cl.
    *B01D 61/36*     (2006.01)
    *C07C 7/04*      (2006.01)
    *C07C 7/144*     (2006.01)

(52) U.S. Cl.
    CPC ....... *B01D 61/3641* (2022.08); *B01D 61/366* (2013.01); *C07C 7/04* (2013.01);
    (Continued)

(58) Field of Classification Search
    CPC ................ B01D 61/364; B01D 61/366; B01D 2311/04; B01D 2311/06;
    (Continued)

(56) References Cited

U.S. PATENT DOCUMENTS

2004/0215045 A1    10/2004 Herrera et al.
2006/0281960 A1    12/2006 Jolimaitre et al.

OTHER PUBLICATIONS

Park et al., "Performance Study of Multistage Membrane and Hybrid Distillation Processes for Propylene/Propane Separation", The Canadian Journal of Chemical Engineering, vol. 95, Dec. 2017, pp. 2390-2397.

(Continued)

*Primary Examiner* — Thuan D Dang
(74) *Attorney, Agent, or Firm* — Baker & McKenzie LLP

(57) ABSTRACT

The present invention relates to an olefins-paraffins separation process in feed stream containing hydrocarbons with 2 to 4 carbon atoms by facilitated transport membrane specific to olefins, comprising a step (a) of feeding the feed stream containing hydrocarbons with 2 to 4 carbon atoms into distillation column and at least 1 stage of membrane unit connected to distillation column at the feed of distillation column and at least 1 stage of membrane unit connected to the side draw of distillation column and a step (b) of separating a portion of feed stream that is passed from the membrane unit, at least 1 stream is the product stream that mostly comprising olefins and at least 1 stream that mostly comprising paraffins.

16 Claims, 4 Drawing Sheets

(52) U.S. Cl.
CPC .......... *C07C 7/144* (2013.01); *B01D 2311/04* (2013.01); *B01D 2311/06* (2013.01); *B01D 2311/2669* (2013.01); *B01D 2317/025* (2013.01)

(58) Field of Classification Search
CPC ...... B01D 2311/2669; B01D 2317/025; B01D 3/145; C07C 7/04; C07C 7/144
See application file for complete search history.

(56) References Cited

OTHER PUBLICATIONS

International Preliminary Report on Patentability dated Jun. 22, 2021 in connection with International Application No. PCT/TH2020/000016, 24 pages.
International Search Report and Written Opinion dated Nov. 30, 2020 in connection with International Application No. PCT/TH2020/000016, 9 pages.

OLEFINS-PARAFFINS SEPARATION PROCESS BY MEMBRANE

CROSS-REFERENCE TO RELATED APPLICATIONS

This application is a continuation of and claims priority to International Application No. PCT/TH2019/000016, filed on Mar. 17, 2020, titled "Olefins-Paraffins Separation Process by Membrane," which claims priority to Thailand Application No. 1901001970 filed on Mar. 29, 2019, both of which are incorporated by reference in their entirety for all purposes.

FIELD OF THE INVENTION

Chemical engineering relates to the olefins-paraffins separation process by membrane.

BACKGROUND OF THE INVENTION

The olefins hydrocarbon separation process in the olefins-paraffins hydrocarbon feed stream having similar number of carbon atom is normally operated by distillation which is the conventional method employing very high reflux ratio because the substances to be separated has close relative volatility, causes said separation process need very high energy. Therefore, there have been studies in the use of membrane in the distillation process in order to increase separation efficiency for the olefins product and decrease energy consumption. However, the number of stage of the membrane unit and the installation position of the membrane unit affects the separation efficiency of product and the energy saving efficiency. The installation of the membrane unit at one or two positions connected to the feed stream, top stream, bottom stream, or recycle stream of the distillation column gives low production capacity and separation efficiency, and the obtained energy saving efficiency is also not very well.

Until present, there are several reports about the separation process of the hydrocarbon compounds having close boiling points. For example, US patent document no 2006/0281960 A1 discloses the separation process of the hydrocarbon compounds having close boiling points and the installation of the membrane in order to separate at least one n-paraffin from the hydrocarbon feed having 4 to 16 carbon atoms. Said separation process is obtained from the feeding of the feed into at least one distillation column and at least one membrane unit. Said membrane is specific to at least one n-paraffin. Then, at least one separated substance is fed back into the separation process in which the membrane unit is connected to the feed, top, bottom or side draw position of the distillation column, wherein one distillation column can be installed with several membrane units in several positions.

US patent document no 2006/0047176 A1 discloses the production of butene from metathesis reaction, comprising the feeding of the feed having 4 carbon atoms containing paraffins and olefins into the fractional separation process in order to separate substance into 2 streams. The first stream contains 1-butene and the second stream contains 2-butene. Then, one part of 2-butene is transformed into 1-butene by isomerization reaction of the second stream. At least one part of the isomerization residue of the second stream is recycled into the previous fractional separation process. At least one feed having 4 carbon atoms and the second stream is fed through the facilitated transport membrane for further removing butane.

US patent document no 2018/0029958 A1 discloses the separation process of the feed having 4 carbon atoms comprising isobutylene, 1-butene, 2-butene, n-butane, and isobutane. Said separation process is operated by extractive distillation using organonitrile, semi-permeate membrane, and combination thereof. The separated olefins are fed back into the production process to transform at least one 2-butene into 1-butene product by isomerization reaction in order to obtain at least 80% by weight of 1-butene product.

From the reasons mentioned above, this invention aims to develop the installation of membrane unit in single stage or multi-stages in series connected to the feed and the side draw of the distillation column in order to increase the production capacity and the separation efficiency of olefins product. Moreover, this invention also aims to reduce the energy consumption in the olefins-paraffins separation process.

SUMMARY OF INVENTION

The present invention relates to an olefins-paraffins separation process in feed stream containing hydrocarbons with 2 to 4 carbon atoms by facilitated transport membrane installed in single stage or multi-stage in series, connected to the feed and the side draw of the distillation column in order to increase the production capacity and the separation efficiency of the olefins products, including the reduction of the energy consumption for the olefins-paraffins separation process.

In one aspect, said olefins-paraffins separation process comprising the following steps:
a. feeding the feed stream containing hydrocarbons with 2 to 4 carbon atoms into distillation column and membrane unit, characterized in that said membrane unit comprising at least 1 stage of the membrane unit connected to the distillation column at the feed of the distillation column and at least 1 stage of the membrane unit connected to the side draw of the distillation column, wherein said membrane unit comprising membrane that is specific for olefins; and
b. separating one part of feed stream that is passed from the membrane unit, wherein at least 1 stream is the product stream that mostly comprising olefins and at least 1 stream that mostly comprising paraffins.

DESCRIPTION OF THE INVENTION

Definition

Figure 1:
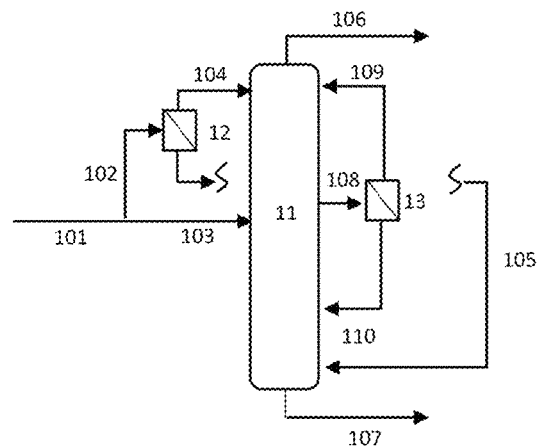
FIG. 1 shows the olefins-paraffins separation process according to the invention 1, having 1 stage of the membrane unit installed connecting to the feed and the side draw of the distillation column.

Technical terms or scientific terms used here have definitions as by person skilled in the art unless stated otherwise.

Any tools, equipment, methods, or chemicals named here mean tools, equipment, methods, or chemicals being used commonly by person skilled in the art unless stated otherwise that they are tools, equipment, methods, or chemicals specific only in this invention.

Use of singular noun or singular pronoun with "comprising" in claims or specification means "one" and including "one or more", "at least one", and "one or more than one" too.

All compositions and/or methods disclosed and claims in this application aim to cover embodiments from any action, performance, modification, or adjustment without any experiment that significantly different from this invention, and obtain with object with utility and resulted as same as the present embodiment according to person ordinary skilled in the art although without specifically stated in claims. Therefore, substitutable or similar object to the present embodiment, including any little modification or adjustment that clearly seen by person skilled in the art should be construed as remains in spirit, scope, and concept of invention as appeared in appended claims.

Throughout this application, term "about" means any number that appeared or showed here that could be varied or deviated from any error of equipment, method, or personal using said equipment or method, including variations or variances occurred from changes of reaction conditions according to uncontrollable parameters such as humidity and temperature.

Hereafter, invention embodiments are shown without any purpose to limit any scope of the invention.

This invention relates to the olefins-paraffins separation process in feed stream containing hydrocarbons with 2 to 4 carbon atoms, comprising the following step:

a. feeding the feed stream containing hydrocarbons with 2 to 4 carbon atoms into distillation column and membrane unit, characterized in that said membrane unit comprising at least 1 stage of the membrane unit connected to the distillation column at the feed of the distillation column and at least 1 stage of the membrane unit connected to the side draw of the distillation column, wherein said membrane unit comprising membrane that is specific for olefins; and b. separating one part of feed stream that is passed from the membrane unit, wherein at least 1 stream is the product stream that mostly comprising olefins and at least 1 stream that mostly comprising paraffins.

In one embodiment, said membrane unit comprising at least 1 stage of the membrane unit which connected to the distillation column at the feed of the distillation column, and at least 1 stage of the membrane unit which connected to the distillation column at the side draw of the distillation column.

Preferably, said membrane unit is the membrane unit comprising at least 2 stages in series which connected to the distillation column at the feed of the distillation column, and at least 2 stages in series which connected to the distillation column at the side draw of the distillation column.

Most preferably is 2 to 5 stages in series of the membrane unit which connected to the distillation column at the feed of the distillation column, and 2 to 5 stages in series of the membrane unit which connected to the distillation column at the side draw of the distillation column.

In one embodiment, said membrane unit comprises the facilitated transport membrane which is specific to olefins.

In one embodiment, said membrane unit comprises the polysaccharide material which is fixed by the metal selected from silver, copper, or the combination thereof. Preferably is fixed by the metal selected from silver.

In one embodiment, the feed stream of said olefins-paraffins separation process is selected from hydrocarbon compounds having 2 to 4 carbon atoms, preferably is the hydrocarbon compounds having 4 carbon atoms.

In one embodiment, said feed stream comprising 5 to 95% by weight of olefins hydrocarbon and 5 to 95% by weight of paraffins hydrocarbon. Preferably comprises 20 to 30% by weight of olefins hydrocarbon and 70 to 80% by weight of paraffins hydrocarbon.

In one embodiment, said feed stream contains olefins selected from butene-1, butene-2, or mixture thereof, and paraffins are n-butane.

In one embodiment, said hydrocarbons feed stream is fed into 1 stage of the membrane unit connected to the distillation column at the feed of the distillation column, and after being fed through the membrane unit, will be separated into a permeate stream and a retentate stream that will be fed back into the distillation column at different positions, and wherein at the side draw of the distillation column, the feed stream will be draw off to feed into 1 stage of the membrane unit connected to the distillation column at the side draw of the distillation column, and after being fed through the membrane unit, it will be separated into a permeate stream and a retentate stream that will be fed back into the distillation column at different positions.

Preferably, said hydrocarbons feed stream is fed into 2 or more stages of the membrane unit connected in series, which connected to the distillation column at the feed of the distillation column, and when being fed through the membrane unit, it will be separated into a permeate stream and a retentate stream, wherein the permeate stream will be fed back into the distillation column or being combined to the previous permeate stream through the previous stage of the membrane unit back into the distillation column, and the retentate stream will be fed into the next stage of the membrane unit connected in series, and wherein at the side draw of the distillation column, the feed stream is fed into 2 or more stages of the membrane unit connected in series, which connected to the distillation column at the side draw of the distillation column, and when being fed through the membrane unit, it will be separated into a permeated stream and a retentate stream, wherein the permeate stream will be fed back into the distillation column or being combined to the previous permeate stream through the previous stage of the membrane unit back into the distillation column, and the retentate stream will be fed into the next stage of the membrane unit connected in series.

Most preferably, said hydrocarbons feed stream is fed into 2 to 5 stages of the membrane unit connected in series, which connected to the distillation column at the feed of the distillation column, and when being fed through the membrane unit, it will be separated into a permeate stream and a retentate stream, wherein the permeate stream will be fed back into the distillation column or being combined to the previous permeate stream through the previous stage of the membrane unit back into the distillation column, and the retentate stream will be fed into the next stage of the membrane unit connected in series, and wherein at the side draw of the distillation column, the feed stream is fed into 2 to 5 stages of the membrane unit connected in series, which connected to the distillation column at the side draw of the distillation column, and when being fed through the membrane unit, it will be separated into a permeate stream and a retentate stream, wherein the permeate stream will be fed back into the distillation column or being combined to the previous permeate stream through the previous stage of the membrane unit back into the distillation column, and the retentate stream will be fed into the next stage of the membrane unit connected in series.

In one embodiment, said permeate stream through the membrane is fed into the distillation column at the position that the composition of an inside stream that travels through said distillation column is similar to the composition of the permeate stream that is fed through the membrane, or having equal or less olefins concentration, and the retentate stream is fed into the distillation column at the position that the composition of an inside stream that travels through said distillation column is similar to the composition of the retentate stream, or having equal or less paraffins concentration.

In one embodiment, the reflux ratio of the feed stream to the distillation column is between 3 to 200.

In one embodiment, the weight ratio of the retentate stream which is fed into any stage of the membrane unit to the amount of the retentate stream being fed into the previous stage of the membrane unit is 50% or more.

In another embodiment, said olefins-paraffins separation process is operated in the distillation column having 80 to 200 theoretical stages at the temperature between 30 to 70° C. and the pressure between 1 to 6.5 bars. Preferably are 120 to 180 theoretical stages at the temperature between 30 to 60° C. and the pressure between 1 to 5 bars. Most preferably are 160 to 170 theoretical stages at the temperature between 30 to 50° C. and the pressure between 2 to 5 bars.

In another embodiment, said olefins-paraffins separation process reduces the energy consumption 30 to 50% comparing to the separation process according to the prior art that has no membrane unit installed.

In another embodiment, said olefins-paraffins separation process increases the production capacity at least 30% comparing to the separation process according to the prior art that has no membrane unit installed.

Figure 3:
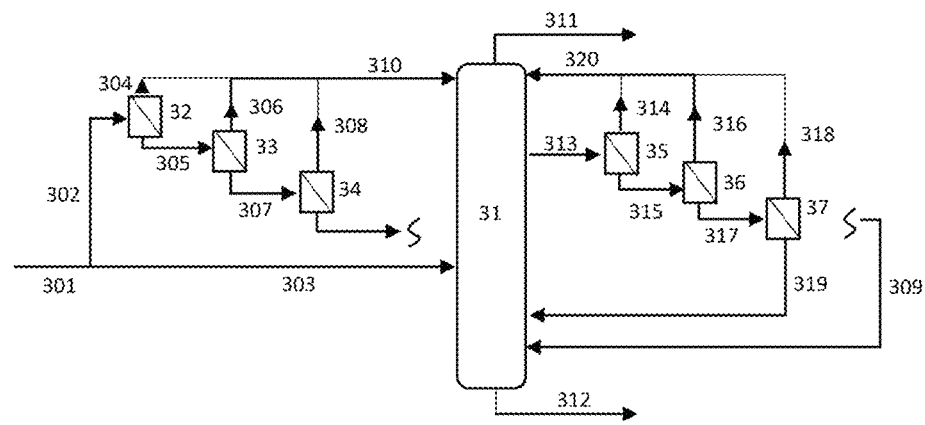
FIG. 3 shows the olefins-paraffins separation process according to the invention 3, having 3 stages of the membrane unit installed connecting to the feed and the side draw of the distillation column.
Figure 4:
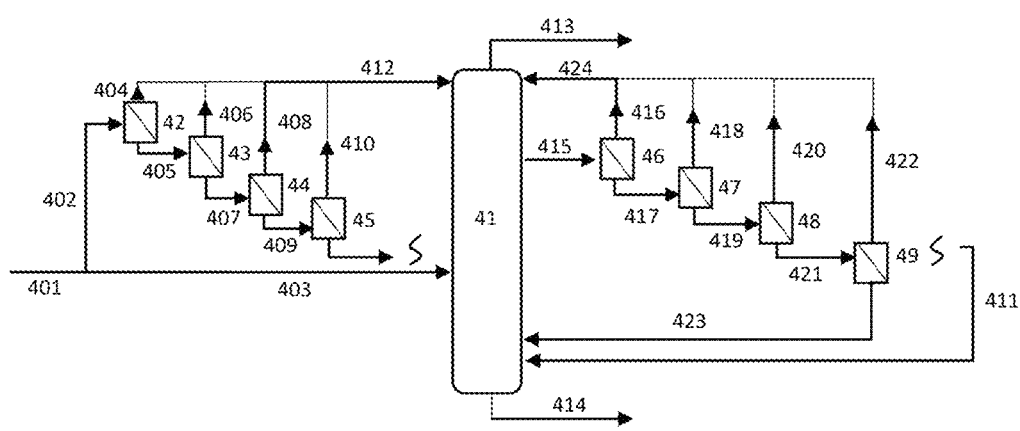
FIG. 4 shows the olefins-paraffins separation process according to the invention 4, having 4 stages of the membrane unit installed connecting to the feed and the side draw of the distillation column.
Figure 5:
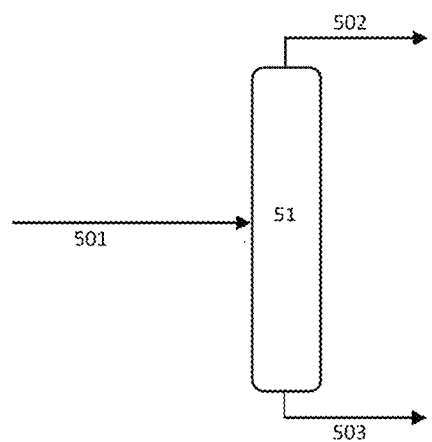
FIG. 5 shows the olefins-paraffins separation process according to the prior art, having no membrane unit installed.
Figure 6:
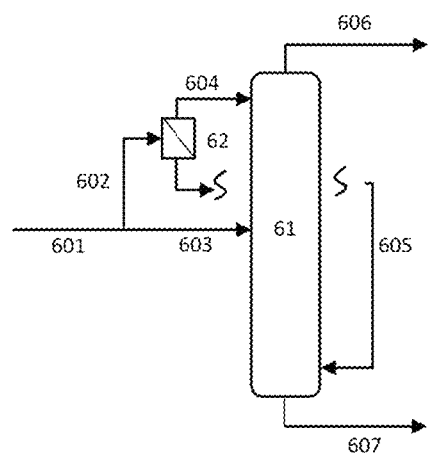
FIG. 6 shows the olefins-paraffins separation process according to the prior art, having 1 stage of the membrane unit installed connecting to the feed of the distillation column.
Figure 7:
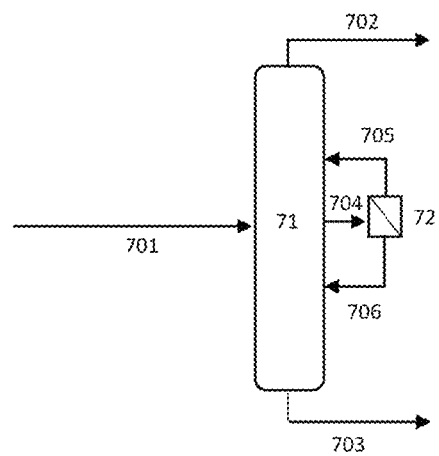
FIG. 7 shows the olefins-paraffins separation process according to the prior art, having 1 stage of the membrane unit installed connecting to the side draw of the distillation column.

In order to compare the efficiency of the olefins-paraffins separation process having membrane unit installation pattern according to the present invention to the olefins-paraffins separation process according to the prior art having no membrane unit installed, the olefins-paraffins separation process having at least 1 membrane unit connected to the feed and the side draw of the distillation column according to the invention in FIG. 1, FIG. 2, FIG. 3, and FIG. 4, and the olefins-paraffins separation process according to the prior art having no membrane unit installed or having 1 stage of the membrane unit connected to the distillation column at the feed or the side draw of the distillation column in FIG. 5, FIG. 6, and FIG. 7 were carried out and tested by using Aspen Plus Simulation Software. Details are as the followings.

The olefins-paraffins separation process could be done by feeding the feed stream containing hydrocarbon compounds having 4 carbon atoms through the membrane unit comprising the facilitated transport membrane connected to the feed and the side draw of the distillation column. The distillation column had 160 to 170 stages. Temperature was between 30 to 50° C. Pressure was between 2 to 5 bars.

Said feed stream contained the olefins hydrocarbon compound between 20 to 30% by weight, comprising butene-1 and butene-2 and paraffins which were n-butane in the amount of between 70 to 80% by weight.

The Olefins-Paraffins Separation Process According to the Invention

The Olefins-Paraffins Separation Process 1

The olefins-paraffins separation process 1 is shown in FIG. 1. It was done by separating the feed stream of hydrocarbon compounds (101) into 2 streams which were the feed stream to the membrane unit (102) and the feed stream to the distillation column (103). The feed stream to the membrane unit (102) was fed through the membrane unit (12) comprising 1 stage of the membrane unit connected to the distillation column (11) at the feed of the distillation column (11). When the feed stream to the membrane unit (102) was fed through the membrane unit (12), it was separated into the permeate stream (104) mostly comprising olefins and the retentate stream (105) mostly comprising paraffins. The permeate stream (104) was fed into the distillation column (11) at the position that the composition of an inside stream that travels through said distillation column (11) is close to the composition of the permeate stream (104), or having equal or less olefins concentration. The retentate stream (105) was fed into the distillation column (11) at the position that the composition of an inside stream that travels through said distillation column (11) is close to the composition of the retentate stream (105), or having equal or less paraffins concentration.

At the side draw of the distillation column (11), the feed stream (108) was fed into the membrane unit (13) comprising 1 stage of the membrane unit connected to the distillation column at the side draw of the distillation column. When it was fed through the membrane unit (13), it was separated into the permeate stream (109) mostly comprising olefins and the retentate stream (110) mostly comprising paraffins. The permeate stream (109) was fed into the distillation column (11) at the position that the composition of an inside stream that travels through said distillation column (11) is close to the composition of the permeate stream (109), or having equal or less olefins concentration. The retentate stream (110) was fed into the distillation column (11) at the position that the composition of an inside stream that travels through said distillation column (11) is close to the composition of the retentate stream (110), or having equal or less paraffins concentration. The obtained olefins product (106) was fed out at the top of the distillation column (11), and the paraffins hydrocarbon compounds (107) was fed out at the bottom of the distillation column (11).

The Olefins-Paraffins Separation Process 2

Figure 2:
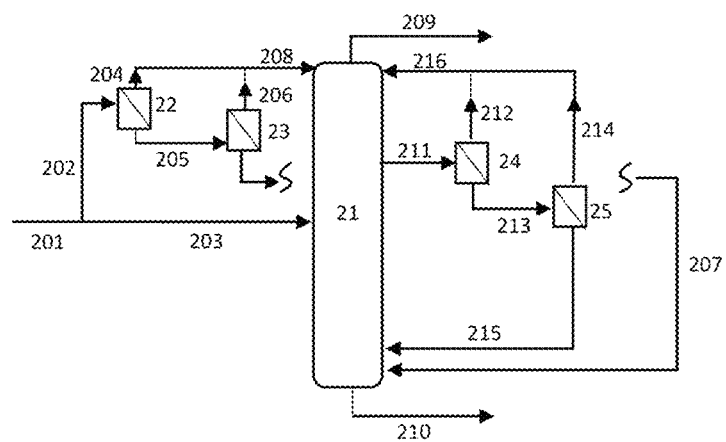
FIG. 2 shows the olefins-paraffins separation process according to the invention 2, having 2 stages of the membrane unit installed connecting to the feed and the side draw of the distillation column.

The olefins-paraffins separation process 2 is shown in FIG. 2. It was done by separating the feed stream of hydrocarbon compounds (201) into 2 streams which were the feed stream to the membrane unit (202) and the feed stream to the distillation column (203). The feed stream to the membrane unit (202) was fed through the membrane unit comprising 2 stages of the membrane unit which were the membrane unit (22) and (23) connected to the distillation column (21) at the feed of the distillation column (21). When the feed stream to the membrane unit (202) was fed through the membrane unit (22), it was separated into the permeate stream (204) mostly comprising olefins and the retentate stream (205) mostly comprising paraffins. The permeate stream (204) was fed into the distillation column (21) at the position that the composition of an inside stream that travels through said distillation column (21) is close to the components of the permeate stream (204), or having equal or less olefins concentration. The retentate stream (205) was fed into the membrane unit (23) and was separated into the permeate stream (206) mostly comprising olefins, and the retentate stream (207) mostly comprising paraffins. The permeate stream (206) was combined to the permeate stream (204) to be the stream (208) and was fed back into the distillation column (21) at the position that the composition of an inside stream that travels through said distillation column (21) is close to the composition of the permeate stream (206) or having equal or less olefins concentration. The retentate stream (207) was fed into the distillation column (21) at the position that the composition of an inside stream that travels through said distillation column (21) is close to the composition of the retentate stream (207), or having equal or less paraffins concentration.

At the side draw of the distillation column (21), the feed stream (211) was fed into the membrane unit comprising 2 stages of the membrane unit (24) and (25) connected to the distillation column (21) at the side draw of the distillation column. When the feed stream (210) was fed through the membrane unit (24), it was separated into the permeate stream (212) mostly comprising olefins and the retentate stream (213) mostly comprising paraffins. The permeate stream (212) was fed into the distillation column (21) at the position that the composition of an inside stream that travels through said distillation column (21) is close to the composition of the permeate stream (212), or having equal or less olefins concentration. The retentate stream (213) was fed into the membrane unit (25) and was separated into the permeate stream (214) mostly comprising olefins, and the retentate stream (215) mostly comprising paraffins. The permeate stream (214) was combined to the permeate stream (212) to be the stream (216) and was fed back into the distillation column (21) at the position that the composition of an inside stream that travels through said distillation column (21) is close to the composition of the permeate stream (214) or having equal or less olefins concentration. The retentate stream (215) was fed into the distillation column (21) at the position that the composition of an inside stream that travels through said distillation column (21) is close to the composition of the retentate stream (215), or having equal or less paraffins concentration. The obtained olefins product (209) was fed out at the top of the distillation column (21), and the paraffins hydrocarbon compounds (210) was fed out at the bottom of the distillation column (21).

The Olefins-Paraffins Separation Process 3

The olefins-paraffins separation process 3 is shown in FIG. 3. It had 3 stages of the membrane unit connected to the distillation column at the feed of the distillation column, and 3 stages of the membrane unit connected to the distillation column at the side draw of the distillation column.

The Olefins-Paraffins Separation Process 4

The olefins-paraffins separation process 4 is shown in FIG. 4. It had 4 stages of the membrane unit connected to the distillation column at the feed of the distillation column, and 4 stages of the membrane unit connected to the distillation column at the side draw of the distillation column.

The Olefins-Paraffins Separation Process According to the Prior Art

The Olefins-Paraffins Separation Process 5

The olefins-paraffins separation process 5 is shown in FIG. 5. It was the olefins-paraffins separation process according to the prior art having no membrane unit installed.

The Olefins-Paraffins Separation Process 6

The olefins-paraffins separation process 6 is shown in FIG. 6. It had 1 stage of the membrane unit connected to the distillation column at the feed of the distillation column.

The Olefins-Paraffins Separation Process 7

The olefins-paraffins separation process 7 is shown in FIG. 7. It had 1 stage of the membrane unit connected to the distillation column at the side draw of the distillation column.

TABLE 1

The mass balance obtained from the olefins-paraffins separation process 1 model

| % Mass ratio | Stream 101 | Reflux | Stream 102 | Stream 104 | Stream 105 | Stream 106 | Stream 107 | Stream 108 | Stream 109 | Stream 110 |
| --- | --- | --- | --- | --- | --- | --- | --- | --- | --- | --- |
| Butene-1 | 5.0 | 99.9 | 5.0 | 30.0 | 3.0 | 99.9 | 2.0 | 3.0 | 22.0 | 2.0 |
| Butene-2 | 20.0 | 0.1 | 20.0 | 69.0 | 16.0 | 0.1 | 16.0 | 21.0 | 77.0 | 16.0 |
| n-butane | 75.0 | 0.0 | 75.0 | 1.0 | 81.0 | 0.0 | 82.0 | 76.0 | 1.0 | 82.0 |
| Mass flow rate (kg/hr) | 49,000 | 160,000 | 12,500 | 1,000 | 11,500 | 2,000 | 47,000 | 10,000 | 700 | 9,300 |

TABLE 2

The mass balance obtained from the olefins-paraffins separation process 2 model

| % Mass ratio | Stream 201 | Reflux | Stream 202 | Stream 208 | Stream 207 | Stream 209 | Stream 210 | Stream 211 | Stream 216 | Stream 215 |
|---|---|---|---|---|---|---|---|---|---|---|
| Butene-1 | 5.0 | 99.9 | 5.0 | 29.3 | 2.1 | 99.9 | 1.3 | 4.7 | 25.5 | 1.9 |
| Butene-2 | 20.0 | 0.1 | 20.0 | 69.7 | 13.7 | 0.1 | 21.3 | 21.7 | 73.5 | 14.6 |
| n-butane | 75.0 | 0.0 | 75.0 | 1.0 | 84.2 | 0.0 | 77.4 | 73.6 | 1.0 | 83.5 |
| Mass flow rate (kg/hr) | 49,000 | 130,000 | 12,500 | 1,500 | 11,000 | 2,000 | 47,000 | 10,000 | 1,200 | 8,800 |

TABLE 3

The mass balance obtained from the olefins-paraffins separation process 3 model

| % Mass ratio | Stream 301 | Reflux | Stream 302 | Stream 310 | Stream 309 | Stream 311 | Stream 312 | Stream 313 | Stream 320 | Stream 319 |
|---|---|---|---|---|---|---|---|---|---|---|
| Butene-1 | 5.0 | 99.9 | 5.0 | 28.5 | 1.5 | 99.9 | 1.5 | 5.0 | 25.2 | 1.5 |
| Butene-2 | 20.0 | 0.1 | 20.0 | 70.5 | 12.1 | 0.1 | 12.1 | 22.7 | 73.8 | 13.5 |
| n-butane | 75.0 | 0.0 | 75.0 | 1.0 | 86.4 | 0.0 | 86.4 | 72.3 | 1.0 | 85.0 |
| Mass flow rate (kg/hr) | 49,000 | 117,000 | 12,500 | 1,700 | 10,800 | 2,000 | 47,000 | 10,000 | 1,500 | 8,500 |

TABLE 4

The mass balance obtained from the olefins-paraffins separation process 4 model

| % Mass ratio | Stream 401 | Reflux | Stream 402 | Stream 412 | Stream 411 | Stream 413 | Stream 414 | Stream 415 | Stream 424 | Stream 423 |
|---|---|---|---|---|---|---|---|---|---|---|
| Butene-1 | 5.0 | 99.9 | 5.0 | 28.0 | 1.2 | 99.9 | 1.2 | 5.1 | 24.6 | 1.2 |
| Butene-2 | 20.0 | 0.1 | 20.0 | 71.0 | 11.1 | 0.1 | 11.1 | 23.3 | 74.4 | 12.7 |
| n-butane | 75.0 | 0.0 | 75.0 | 1.0 | 87.7 | 0.0 | 87.7 | 71.6 | 1.0 | 86.1 |
| Mass flow rate (kg/hr) | 49,000 | 112,500 | 12,500 | 1,900 | 10,600 | 2,000 | 47,000 | 10,000 | 1,700 | 8,300 |

TABLE 5

The mass balance obtained from the olefins-paraffins separation process 5 model

| % Mass ratio | Stream 501 | Reflux | Stream 502 | Stream 503 |
|---|---|---|---|---|
| Butene-1 | 5.0 | 99.9 | 99.9 | 2.0 |
| Butene-2 | 20.0 | 0.1 | 0.1 | 16.0 |
| n-butane | 75.0 | 0.0 | 0.0 | 82.0 |
| Mass flow rate (kg/hr) | 49,000 | 236,000 | 2,000 | 47,000 |

TABLE 6

The mass balance obtained from the olefins-paraffins separation process 6 model

| % Mass ratio | Stream 601 | Reflux | Stream 602 | Stream 604 | Stream 605 | Stream 606 | Stream 607 |
|---|---|---|---|---|---|---|---|
| Butene-1 | 5.0 | 99.9 | 5.0 | 30.0 | 3.0 | 99.9 | 2.0 |
| Butene-2 | 20.0 | 0.1 | 20.0 | 69.0 | 16.0 | 0.1 | 16.0 |
| n-butane | 75.0 | 0.0 | 75.0 | 1.0 | 81.0 | 0.0 | 82.0 |
| Mass flow rate (kg/hr) | 49,000 | 200,000 | 12,500 | 1,000 | 11,500 | 2,000 | 47,000 |

TABLE 7

The mass balance obtained from the olefins-paraffins separation process 7 model

| % Mass ratio | Stream 701 | Reflux | Stream 702 | Stream 703 | Stream 704 | Stream 705 | Stream 706 |
|---|---|---|---|---|---|---|---|
| Butene-1 | 5.0 | 99.9 | 99.9 | 2.0 | 3.0 | 22.0 | 2.0 |
| Butene-2 | 20.0 | 0.1 | 0.1 | 16.0 | 21.0 | 77.0 | 16.0 |
| n-butane | 75.0 | 0.0 | 0.0 | 82.0 | 76.0 | 1.0 | 82.0 |
| Mass flow rate (kg/hr) | 49,000 | 171,000 | 2,000 | 47,000 | 10,000 | 700 | 9,300 |

The compositions of the substances in the feed streams and the product streams and mass flow rate are shown in table 1 to table 7.

TABLE 8

Test result obtained from the models of the olefins-paraffins separation process according to the invention and the olefins-paraffins separation process according to the prior art installed with single membrane unit at the feed or the side draw of the distillation column comparing to the olefins-paraffins separation process having no membrane unit installed

| | Olefins-paraffins separation process 1 | Olefins-paraffins separation process 2 | Olefins-paraffins separation process 3 | Olefins-paraffins separation process 4 | Olefins-paraffins separation process 6 | Olefins-paraffins separation process 7 |
|---|---|---|---|---|---|---|
| % Olefin recovery | 28 | 44 | 55 | 62 | 28 | 28 |
| % Power saving | 33 | 43 | 47 | 49 | 15 | 23 |

The olefins separation efficiency and the energy saving efficiency in the olefins-paraffins separation processes according to the invention and the olefins-paraffins separation processes according to the prior art having single membrane unit installed at the feed or the side draw of the distillation column comparing to the olefins-paraffins separation process according to the prior art having no membrane unit installed are shown in table 8.

When comparing results from the models of the olefins-paraffins separation process according to the present invention to the olefins-paraffins separation process having no membrane unit installed, it was found that the olefins-paraffins separation process according to the present invention could increase the olefins separation efficiency better than the olefins-paraffins separation process according to the prior art having no membrane unit installed or having single membrane unit installed at the feed or the side draw of the distillation column. The olefins-paraffins separation process according to the present invention having membrane units installed could increase the olefins recovery percentage to feed back into the distillation column correlated to the number of membrane unit stage installed, which was correlated to the reduced energy consumption in the olefins-paraffins separation process.

From the results above, it can be said that the olefins-paraffins separation process according to the present invention has high efficiency and can increase the production capacity and the olefins recovery percentage. This also reduces the energy consumption as indicated in the objective of this invention.

BEST MODE OF THE INVENTION

Best mode of the invention is as provided in the detailed description of the invention.

The invention claimed is:

1. An olefins-paraffins separation process in feed stream containing hydrocarbons with 2 to 4 carbon atoms, comprising the following step:
    a. feeding the feed stream containing hydrocarbons with 2 to 4 carbon atoms into distillation column and membrane unit, characterized in that said membrane unit comprising at least 2 stages of the membrane unit connected to the distillation column at the feed of the distillation column and at least 2 stages of the membrane unit connected to the side draw of the distillation column, wherein said membrane unit comprising membrane that is specific for olefins; and
    b. separating a portion of feed stream that is passed from the membrane unit, wherein at least 1 stream is the product stream that mostly comprising olefins and at least 1 stream that mostly comprising paraffins;
    wherein said membrane unit comprises the facilitated transport membrane; and
    wherein the weight ratio of the retentate stream which is fed into any stage of the membrane unit to the amount of the retentate stream which is fed into the previous stage of the membrane unit is 50% or more.

2. The process according to claim 1, wherein said membrane unit comprising 2 to 5 stages of the membrane unit connected in series which connected to the distillation column at the feed of the distillation column, and 2 to 5 stages of the membrane unit connected in series which connected to the distillation column at the side draw of the distillation column.

3. The process according to claim 1, wherein said hydrocarbons feed stream is fed into 2 or more stages of the membrane unit connected in series, which connected to the distillation column at the feed of the distillation column, and when being fed through the membrane unit will be separated into a permeate stream and a retentate stream, wherein the permeate stream will be fed back into the distillation column or being combined to the previous permeate stream from the previous stage of the membrane unit back into the distillation column, and the retentate stream will be fed into the next stage of the membrane unit connected in series; and
    wherein at the side draw of the distillation column, the feed stream is draw off to feed into 2 or more stages of the membrane unit connected in series, which connected to the distillation column at the side draw of the distillation column, and when being fed through the membrane unit will be separated into a permeate stream and a retentate stream, wherein the permeate stream will be fed back into the distillation column or being combined to the previous permeate stream from the previous stage of the membrane unit back into the distillation column, and the retentate stream will be fed into the next stage of the membrane unit connected in series.

4. The process according to claim 3, wherein said hydrocarbons feed stream is fed into 2 to 5 stages of the membrane unit connected in series, which connected to the distillation column at the feed of the distillation column, and when being fed through the membrane unit will be separated into a permeate stream and a retentate stream, wherein the permeate stream will be fed back into the distillation column or being combined to the previous permeate stream through the previous stage of the membrane unit back into the distillation column, and the retentate stream will be fed into the next stage of the membrane unit connected in series; and wherein at the side draw of the distillation column, the feed stream is draw off to feed into 2 to 5 stages of the membrane unit connected in series, which connected to the distillation column at the side draw of the distillation column, and when being fed through the membrane unit will be separated into a permeate stream and a retentate stream, wherein the permeate stream will be fed back into the distillation column or being combined to the previous permeate stream through the previous stage of the membrane unit back into the distillation column, and the retentate stream will be fed into the next stage of the membrane unit connected in series.

5. The process according to claim 3, wherein the permeate stream through the membrane is fed into the distillation column at the position that the composition of an inside stream that travels through the distillation column is close to the composition of the permeate stream that is fed through the membrane, or having equal or less olefins concentration, and the retentate stream is fed into the distillation column at the position that the composition of an inside stream that travels through the distillation column is close to the composition of the retentate stream, or having equal or less paraffins concentration.

6. The process according to claim 3, wherein the reflux ratio of the feed stream to the distillation column is between 3 to 200.

7. The process according to claim 1, wherein said membrane unit comprises the polysaccharide material which is fixed by the metal selected from silver, copper, or the combination thereof.

8. The process according to claim 1, wherein said process is operated in the distillation column having 80 to 200 theoretical stages at the temperature between 30 to 70° C. and the pressure between 1 to 6.5 bars.

9. The process according to claim 8, wherein said process is operated in the distillation column having 120 to 180 theoretical stages at the temperature between 30 to 60° C. and the pressure between 1 to 5 bars.

10. The process according to claim 9, wherein said process is operated in the distillation column having 160 to 170 theoretical stages at the temperature between 30 to 50° C. and the pressure between 1 to 5 bars.

11. The process according to claim 1, wherein said feed stream comprises hydrocarbons having 4 carbon atoms.

12. The process according to claim 1, wherein said feed stream comprises 5 to 95% by weight of olefins hydrocarbon and 5 to 95% by weight of paraffins hydrocarbon.

13. The process according to claim 12, wherein said feed stream comprises 20 to 30% by weight of olefins hydrocarbon and 70 to 80% by weight of paraffins hydrocarbon.

14. The process according to claim 12, wherein olefins are selected from butene-1, butene-2, or mixture thereof and paraffins are n-butane.

15. The process according to claim 1, wherein the production capacity from said process is increased at least 30% comparing to the separation process without the membrane unit.

16. The process according to claim 1, wherein the energy consumption from said process is decreased 30 to 50% comparing to the separation process without the membrane unit.

* * * * *